United States Patent [19]

Cucuzza

[11] Patent Number: 5,030,303
[45] Date of Patent: Jul. 9, 1991

[54] METHOD FOR FORMING DISPOSABLE GARMENTS WITH A WASTE CONTAINMENT POCKET

[75] Inventor: Carl C. Cucuzza, Loganville, Ga.

[73] Assignee: Nordson Corporation, Westlake, Ohio

[21] Appl. No.: 387,064

[22] Filed: Jul. 28, 1989

[51] Int. Cl.$^5$ .................... B32B 31/08; A61F 13/15
[52] U.S. Cl. .................... 156/164; 156/204; 156/227; 156/229; 156/290; 156/291; 604/385.2
[58] Field of Search .............. 156/164, 229, 204, 291, 156/227, 201, 290; 604/385.2, 358; 2/76; 239/8, 298

[56] References Cited

U.S. PATENT DOCUMENTS

| | | | |
|---|---|---|---|
| 721,900 | 3/1903 | Lassoe et al. | 239/406 |
| 2,626,424 | 1/1953 | Hawthorne, Jr. | 65/5 |
| 3,690,518 | 9/1972 | Baker et al. | 222/504 |
| 3,764,069 | 10/1973 | Runstadler, Jr. et al. | 239/8 |
| 3,825,379 | 7/1974 | Lohkamp et al. | 425/72.2 |
| 3,841,567 | 10/1974 | Drozek et al. | 239/570 |
| 4,081,301 | 3/1978 | Buell | 156/164 |
| 4,128,667 | 12/1978 | Timson | 427/348 |
| 4,159,199 | 6/1979 | Levecque et al. | 65/5 |
| 4,185,981 | 1/1980 | Ohsato et al. | 65/5 |
| 4,219,157 | 8/1980 | Binoche | 239/296 |
| 4,253,461 | 3/1981 | Strickland et al. | 604/389 |
| 4,411,389 | 10/1983 | Harrison | 239/427.5 |
| 4,492,608 | 1/1985 | Hirsch et al. | 156/467 |
| 4,704,116 | 11/1987 | Enloe | 604/385.2 |
| 4,711,683 | 12/1987 | Merkatoris | 156/164 |
| 4,738,677 | 4/1988 | Foreman | 604/385.2 |
| 4,764,234 | 8/1988 | Smits et al. | 156/244.11 X |
| 4,785,996 | 11/1988 | Ziecker et al. | 239/298 |
| 4,815,660 | 3/1989 | Boger | 239/8 |
| 4,822,435 | 4/1989 | Igaue et al. | 156/164 |
| 4,834,740 | 5/1989 | Suzuki et al. | 156/164 |
| 4,900,384 | 2/1990 | Sanders et al. | 156/204 |

FOREIGN PATENT DOCUMENTS

| | | | |
|---|---|---|---|
| 0282196 | 5/1988 | European Pat. Off. | |
| 0346928 | 6/1989 | European Pat. Off. | |
| 8534594 | 2/1986 | Fed. Rep. of Germany | |
| 1109198 | 8/1984 | U.S.S.R. | 239/290 |
| 1240465 | 6/1986 | U.S.S.R. | 239/290 |

OTHER PUBLICATIONS

Nordson Corporation Technical Publication 43-1-11, issued Mar. 1981, Amherst, Ohio.

*Primary Examiner*—Michael W. Ball
*Assistant Examiner*—Michele K. Yoder
*Attorney, Agent, or Firm*—Wood, Herron & Evans

[57] ABSTRACT

A method and apparatus is disclosed for forming a disposable garment with a waste containment pocket defined by a pair of barrier cuffs located on opposed sides of the centerline of the body contacting layer of the garment inboard of its elasticized leg openings. Each barrier cuff is formed by applying a pattern of adhesive alongside of an elastic member maintained in tension on the body contacting layer or a separate strip of material, and then intermittently diverting the path of the adhesive pattern such as by a jet of air so that the adhesive contacts and bonds the elastic member to the body contacting layer or separate strip at longitudinally spaced locations therealong. When the tension on the elastic member is released, gathers or folds are formed in the barrier cuff at the locations where the elastic member was adhered thereto which help the garment conform to the shape of the wearer and prevent the passage of body exudates to the elasticized leg openings.

13 Claims, 3 Drawing Sheets

METHOD FOR FORMING DISPOSABLE GARMENTS WITH A WASTE CONTAINMENT POCKET

FIELD OF THE INVENTION

This invention relates to the method of manufacturing disposable garments such as disposable diapers or incontinent pads, and, more particularly, to the method of forming such garments with elasticized barrier pockets or cuffs formed from or attached to the body contacting layer of the garment which define a waste containment pocket for body exudates.

BACKGROUND OF THE INVENTION

Disposable, absorbent garments, such as disposable diapers and adult incontinent briefs, have met with widespread use to absorb and contain body exudates and thus prevent soiling or wetting of clothing, bedding and other articles. Commercially available disposable diapers, for example, are unitary preshaped and prefolded garments which include a moisture-impervious backing layer, a body contacting layer or liner and a moisture-absorbent core therebetween. Elasticized leg openings are formed at the sides of the diaper to improve comfort of the garment and its ability to contain body exudates.

One problem with disposable diapers, incontinent briefs and other garments of the type described above is that the elasticized leg openings have not proven to be entirely effective in retaining body exudates, particularly loose or liquified fecal material. It has been found that such material can leak through the elasticized leg openings because the disposable garment fails to constrain the free flow of the exudate material and no structure is provided to hold such material within the body contacting liner of the diaper. As a result, the exudate material tends to float along the liquid receiving surface of the diaper and work its way past the elasticized leg flaps.

This problem has been addressed in improved disposable garments such as disclosed, for example, in U.S. Pat. Nos. 4,704,116 to Enloe and 4,738,677 to Foreman. The disposable garments disclosed in each of these patents include an exudate material containment pocket formed inwardly of the elasticized leg openings on either side of the centerline of the garment. This containment area or pocket is formed by spaced, longitudinally extending barrier cuffs or flaps which are either integrally formed in the body contacting layer of the diaper or formed from separate strips which are adhered to such body contacting layer. If the barrier cuffs are integrally formed in the body contacting layer of the garment, each cuff is formed by folding the body contacting layer upon itself in a longitudinal direction to obtain opposed longitudinal sections of material which are adhered together. One "fold" or barrier cuff is made in the body contacting layer on either side of the centerline of the garment. Alternatively, separate strips of material are folded in half and adhered together to form each barrier cuff, and these cuffs are then bonded to the body contacting layer of the disposable garment on opposite sides of the centerline thereof.

Preferably, an elastic member such as a bead of natural rubber, elastic tape or the like is adhered at longitudinally spaced locations between the opposed sections of material forming the barrier cuffs. These elastic members are bonded in place by ultrasonic bonding, heat/pressure sealing and/or spaced adhesive beads such as disclosed, for example, in U.S. Pat. Nos. 4,081,301 to Buell and 4,253,461 to Strickland et al. The elastic member within each flap or cuff forms gathers therealong where the elastic member is adhered thereto, and these gathers help the barrier cuffs to conform to the shape of the wearer for better fit and to prevent the passage of body exudates to the elasticized leg openings of the garment.

One problem with the barrier cuffs or flaps forming the waste containment pockets in the disposable garments described above involves the manner in which the barrier cuffs or flaps are adhered together and/or to the body contacting layer of the garment. As mentioned above, the opposed material sections forming each barrier cuff or flap must be bonded together and the elastic member associated with each flap must be bonded between such material sections. Whether the barrier cuffs or flaps are integrally formed from the body contacting layer of the disposable garment, or the flaps are separately formed and then adhered to such body contacting layer, continuous or intermittent extruded beads of hot melt adhesive are typically employed to effect a bond therebetween. It has been observed that such adhesive bonding techniques, particularly when employed on the nonwoven, fibrous material utilized in forming the body contacting layer of a disposable garment, often results in the utilization of more adhesive than is required. A relatively thick, extruded bead of hot melt adhesive, whether applied continuously or intermittently, is highly viscous and does not readily spread out over the surface of the material forming the barrier cuffs. Because the strength of the bond produced by hot melt adhesive is dependent to a large extent on the surface area of contact between the material to be bonded, a relatively large amount of adhesive is needed to bond the opposed sections of material forming the barrier cuff and to adhere the elastic member thereto.

Another problem with the formation of the waste containment pocket of such disposable garments is that two separate bonding operations must be conducted to form the barrier cuffs or flaps. In one operation, adhesive or other bonding means is used to adhere the opposed sections of material forming the barrier cuffs. A second operation and/or additional bonding equipment is then required to adhere the elastic member between the sections forming the barrier cuffs or flaps. These two separate bonding operations add expense and difficulty to the manufacturing process.

SUMMARY OF THE INVENTION

It is therefore among the objectives of this invention to provide a method of forming a disposable garment with a waste containment pocket defined by spaced, elasticized barrier cuffs or flaps which reduces the quantity of adhesive required to form the barrier cuffs, which simplifies the manufacturing operation and which reduces the expense of forming the waste containment pocket.

These objectives are accomplished in a method of forming a waste containment pocket in a disposable garment defined by spaced barrier cuffs or flaps in which each barrier cuff is formed in a single bonding operation, with a single adhesive dispenser using a relatively small quantity of adhesive. The adhesive dispenser is effective to apply a controlled, spiral pattern of an elongated adhesive fiber onto a longitudinally extending section of material along one side of an elastic member held in tension atop such material. The spiral pattern of adhesive from such dispenser is intermittently diverted around and/or onto the elastic member so that it adheres to the material at longitudinally spaced locations therealong. The longitudinally extending section of material is subsequently folded upon itself so that it adheres together with the elastic member contained therein to form the barrier cuff. When the tension is removed from the elastic member, it returns to its original length and forms gathers in the barrier cuff at the locations where the elastic member was adhered to the material.

This invention is therefore predicated upon the concept of applying a thin adhesive fiber pattern onto at least one side of a longitudinally extending section of material which is folded to form the sides of a barrier cuff, and adhering an elastic member between the sides of the barrier cuff, in a single operation. One adhesive dispenser is required to apply the pattern of adhesive necessary to adhere the two sides of the barrier cuff together, and the adhesive pattern applied by such dispenser is intermittently diverted onto the elastic member to simultaneously adhere the elastic member of such barrier cuff.

One advantage of this invention is that a relatively small quantity of adhesive is required to effect a bond between the sides of the strip or section of material forming the barrier cuff. In the presently preferred embodiment, an adhesive dispenser is employed of the type disclosed in U.S. Pat. No. 4,785,996. This adhesive dispenser is effective to apply a thin, elongated strand or fiber of adhesive in a spiral spray pattern onto the material forming the barrier cuff. The thin, adhesive strand or fiber covers a relatively large area of the longitudinally extending section or strip of material forming the barrier cuff, and the adhesive fiber is thin compared to a conventional extruded bead of adhesive. As a result, the sides of the barrier cuff are adhered together with an acceptable bond using a lesser quantity of adhesive than would be required with extruded adhesive beads.

Another advantage of the method of this invention is that the elastic member is connected to the barrier cuff in the same operation and by the same dispensing device which adheres the sections of the barrier cuff together. The pattern of adhesive discharged from the dispenser device is temporarily diverted, e.g., by a jet of air or the like, so that it is deposited onto the elastic member. This eliminates a second bonding operation and/or additional equipment to adhere the elastic member in place. The efficiency of manufacture of the waste containment pockets is thus improved and the overall cost of manufacture is reduced.

In one presently preferred embodiment of this invention, the barrier cuffs or flaps defining the waste containment pocket of the disposable garment are integrally formed in the body contacting layer of the garment. In this embodiment, a pair of tensioned, elastic members are laid onto or immediately above a moving section of the body contacting layer of the disposable garment. Two adhesive dispensers are positioned with respect to the body contacting layer so as to apply a spiral pattern of an elongated adhesive fiber alongside and substantially parallel to each elastic member, but not in contact therewith. The adhesive pattern from each dispenser is intermittently diverted onto one of the elastic members so that the elastic members are adhered to the body contacting layer at longitudinally spaced locations therealong. This diversion of the path of the adhesive pattern is accomplished, for example, by impacting the adhesive discharged from each adhesive dispenser with a jet of air before it contacts the body contacting layer.

The longitudinally extending section of the body contacting layer adjacent each elastic member which received the adhesive is then folded over the elastic member onto the section of the body contacting layer on the opposite side of the elastic member. A barrier cuff or flap is thus formed on opposite sides of the centerline of the body contacting layer, each consisting of two longitudinally extending sections of the body contacting layer material with an elastic member therebetween. The elastic member of each barrier cuff is not adhered to the body contacting layer except in those locations where the adhesive was diverted around or onto the elastic member.

When the tension of the elastic members is released, such as by cutting the body contacting layer to length in the course of forming the disposable garment, the elastic members return to their original length and form gathers in the body contacting layer at the locations where it is adhered thereto. The gathers of the two barrier cuffs on either side of the centerline of the body contacting layer are preferably positioned in alignment with one another and in alignment with the elasticized leg openings in the finished disposable garment. These gathers of each barrier cuff aid in resisting passage of body exudates from the center of the disposable garment outwardly toward the elasticized leg openings and also help the garment to conform to the body of the wearer.

In an alternative embodiment of this invention, the barrier cuffs are formed from separate longitudinally extending sections or strips of material and then adhered to the body contacting layer of the disposable garment instead of being integrally formed from the body contacting layer. The individual barrier cuffs are formed in the same manner as described above except that each strip is folded in half over an elastic member located in the middle thereof, and then one folded strip or barrier cuff is adhered to the body contacting layer on opposite sides of the centerline of the disposable garment to form the waste containment pocket.

DESCRIPTION OF THE DRAWINGS

The structure, operation and advantages of the presently preferred embodiment of this invention will become further apparent, upon consideration of the following description taken in conjunction with the accompanying drawings, wherein.

DETAILED DESCRIPTION OF THE INVENTION

Figure 1:
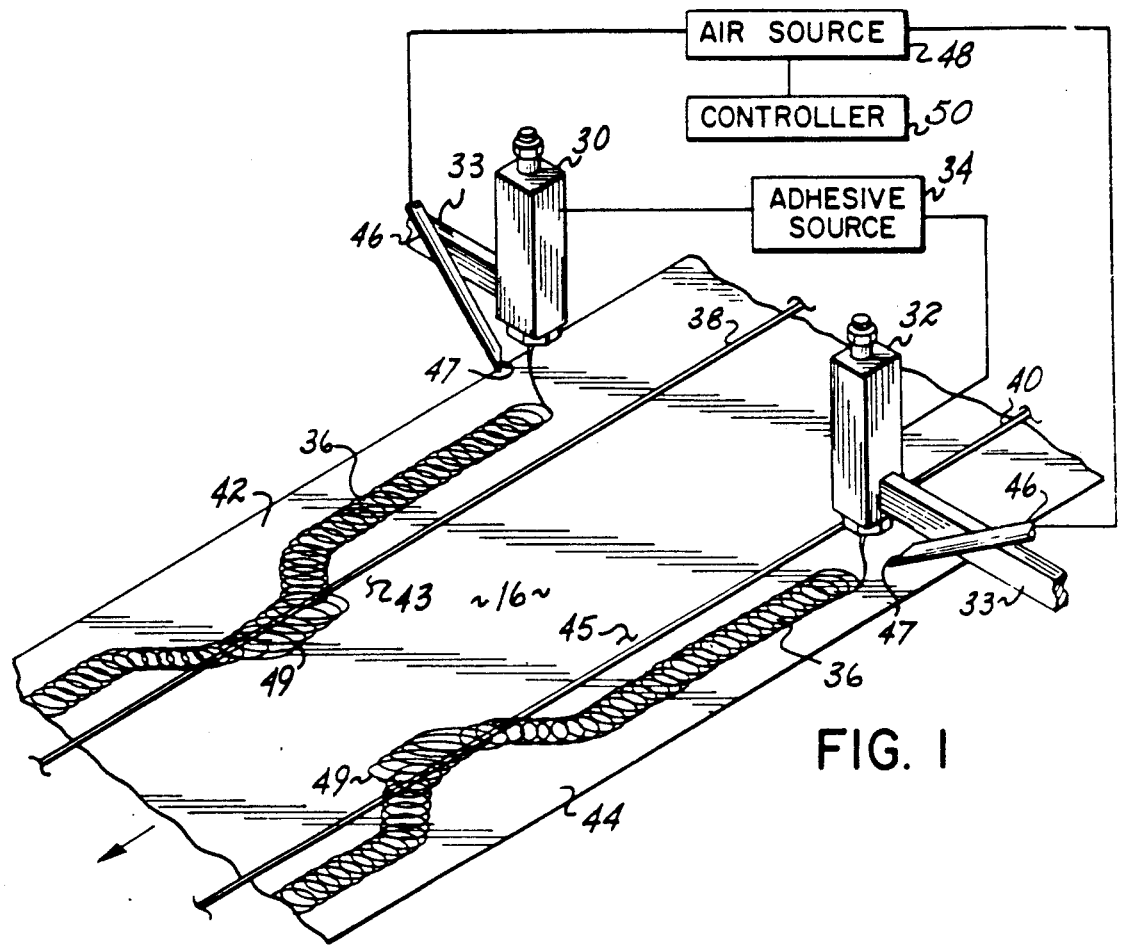
FIG. 1 is a schematic view of the adhesive dispensing devices applying adhesive patterns onto the body contacting layer of a disposable garment.

Referring now to FIGS. 1-4, a method is depicted for forming a waste containment pocket 10 in a disposable garment such as a disposable diaper 12. See FIG. 4. The disposable diaper 12 includes a moisture-impervious backing sheet 14, a body contacting liner or layer 16 and an absorbent, non-woven core or pad 18 therebetween. The diaper 12 is formed with a front waist section 20, a rear waist section 22 and elasticized leg openings 24, 26 on either side of the waste containment pocket 10 which are equidistant from the centerline 28 of the diaper 12.

The method of this invention is directed to the formation of the waste containment pocket 10 which functions to substantially prevent the passage or leakage of body exudates, and particularly loose fecal material, from the center portion of the disposable diaper 12 outwardly and through the elasticized leg openings 24, 26. In the embodiment of FIGS. 1-4, the waste containment pocket 10 is formed as an integral part of the body contacting layer 16. In the embodiment of FIGS. 5-8 discussed below, the waste containment pocket 10 is formed by attaching separate sections to the body contacting layer 16 on either side of the centerline 28 of the disposable diaper 12.

As shown in FIG. 1, a flat sheet of the body contacting layer 16 is movable on a conveyor (not shown) beneath a pair of adhesive dispensing devices 30 and 32 which are each carried by a support 33 and which communicate with an adhesive source 34. Each of the adhesive dispensing devices 30, 32 is of the type disclosed in U.S. Pat. No. 4,785,996 to Ziecker et al, the disclosure of which is incorporated by reference in its entirety herein. The structural details of the dispensing devices 30, 32 form no part of this invention per se, and reference should be made to the U.S. Pat. No. 4,785,996 for the details thereof.

The dispensing devices 30, 32 are each effective to apply a thin, elongated strand or fiber of adhesive in a spiral spray pattern 36 onto the body contacting layer 16. As discussed in detail in the U.S. Pat. No. 4,785,996, a bead of adhesive is extruded from the dispensing devices 30, 32 and impacted with jets of air directed tangentially thereto which attenuate or stretch the adhesive bead forming an elongated strand or fiber which is spun or twisted by the air jets to form the resulting spiral spray pattern 36.

In the presently preferred embodiment, elastic members 38 and 40 are placed onto or immediately above the body contacting layer 16 beneath the dispensing devices 30, 32, respectively. These elastic members 38, 40 are maintained under tension as the body contacting layer 16 passes beneath the dispensing devices 30, 32, but are permitted to retract or move back to their normal length when the tension is released as discussed below. The elastic members 38, 40 are of the type commonly utilized in the elasticized leg openings of disposable diapers and can be formed of such materials as natural rubber, elastic tape, a bead of elastomeric adhesive and the like.

Figure 2:
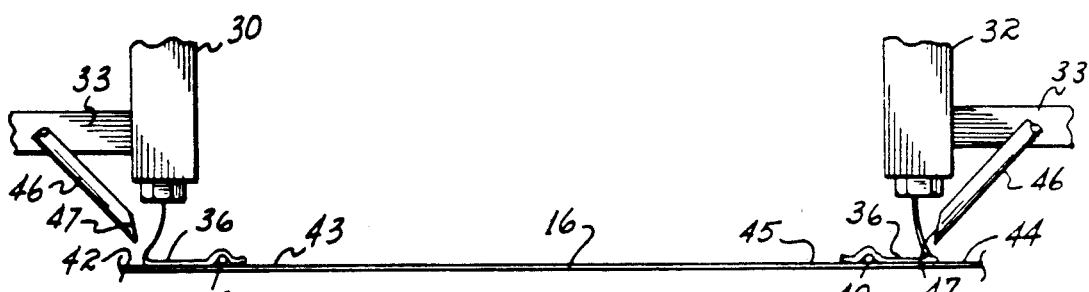
FIG. 2 is a side elevational view of the apparatus of FIG. 1.

As shown in FIGS. 1 and 2, the elastic member 38 is positioned with respect to the dispensing device 30 such that a longitudinally extending spiral spray pattern 36 is applied onto the body contacting layer 16 along one side 42 of the elastic member 38 without contacting the elastic member 38 or the body contacting layer 16 on the other side 43 of the elastic member 38. A second adhesive pattern 36 is applied by the dispensing device 32 on the opposite side of the body contacting layer 16 along one side 44 of the elastic member 40 without contacting the elastic member 40 or the body contacting layer 16 on the opposite side 45 of the elastic member 40.

In the presently preferred embodiment, an air tube 46 is mounted to each support 33 which carries the dispensing devices 30, 32, and these air tubes 44 each have a discharge opening 47 oriented at an angle with respect to the body contacting layer 16. The air tubes 44, 46 are each connected to a source of pressurized air 48, shown schematically in FIG. 1, and are effective to eject a jet of air through their discharge openings 47 against the spray patterns 36. Each jet of air impacts a spiral spray pattern 36 before it contacts the surface of the body contacting layer 16 so that the adhesive patterns 36 are deflected or diverted around and/or onto the elastic members 38 and 40 instead of being applied parallel thereto.

In the presently preferred embodiment, a controller 50 is connected to the pressurized air source 48. The controller 50 is operative to supply pressurized air intermittently or periodically to the air tubes 46 so that the adhesive patterns 36 are intermittently diverted onto the elastic members 38, 40 along the body contacting layer 16. The air jets impact the spray patterns 36 with sufficient velocity to both enlarge the width of such patterns 36, and to cause them to cross over the elastic members 38 and 40 without breaking up. As shown in FIG. 1, one pattern 36 is diverted from the body contacting layer 16 on one side 42 of the elastic member 38 onto and/or around the elastic member 38 and a portion of the body contacting layer 16 on the opposite side 43 of the elastic member 38 at longitudinally spaced areas 49 therealong. Similarly, the other pattern 36 is diverted from the body contacting layer 16 on one side 44 of the elastic member 40 onto and/or around such elastic member 40 and a portion of the body contacting layer 16 on the opposite side 45 of the elastic member 40 at longitudinally spaced areas 49 therealong. The elastic members 38, 40 are therefore adhered to opposite sides of the body contacting layer 16 at such longitudinally spaced areas 49. As discussed in more detail below, the adhesive spray pattern 36 is diverted onto the elastic members 38, 40 wherever pleats or gathers 52 are desired to be formed in the waste containment pocket 10. See FIG. 4.

Figure 3:
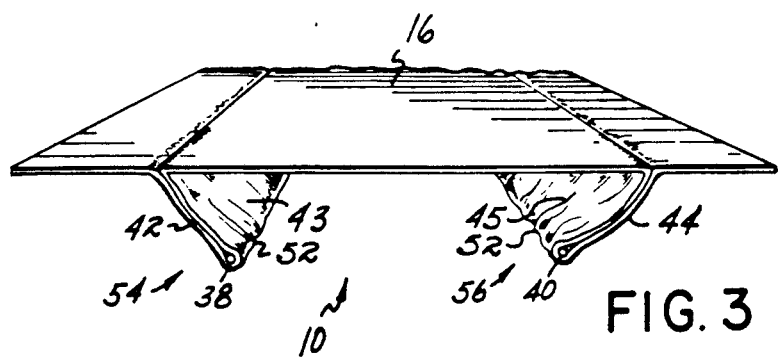
FIG. 3 is a view of the body contacting layer of FIG. 1 which is folded upon itself to form opposed barrier cuffs.
Figure 4:
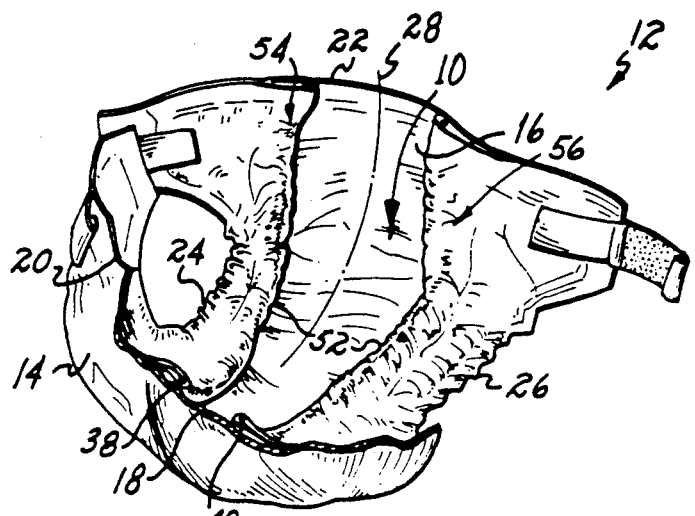
FIG. 4 is a schematic, perspective view in partial cross section of a disposable diaper incorporating the barrier cuffs formed in accordance with the steps illustrated in FIGS. 1-3.

With reference to FIGS. 3 and 4, the waste containment pocket 10 of the disposable diaper 12 is defined by a pair of opposed barrier cuffs or flaps 54 and 56 located on opposite sides of the centerline 28 of the diaper 12 inboard of the elasticized leg openings 24, 26, respectively. In the embodiment of FIGS. 1-4, these barrier cuffs 54 and 56 are integrally formed in the body contacting layer 16 in a folding operation depicted in FIG. 3. After a spiral spray pattern 36 has been applied to opposite sides of the body contacting layer 16, and selected areas 49 of the elastic members 38, 40 have been adhered to the body contacting layer 16, the section 42 of the body contacting layer 16 on the lefthand side of FIG. 1 which received the adhesive pattern 36 is folded over onto the section 43 of the body contacting layer 16 on the opposite side of each elastic member 38 to form barrier cuff 54. Similarly, the section 44 of the body contacting layer 16 on the righthand portion of FIG. 1 which received the adhesive pattern 36 is folded over onto the section 45 on the opposite side of elastic member 40 to form barrier cuff 56. As shown in FIG. 3, the resulting barrier cuffs 54, 56 comprise opposed sides 42, 43 and 44, 45 respectively, with an elastic member 38 or 40 therebetween. When the body contacting layer 16 is adhered to the remaining elements of the disposable diaper 12 as shown in FIG. 4, these barrier cuffs 54 and 56 are located on opposite sides of the centerline 28 of the diaper 12 to define the waste containment pocket 10 and are spaced inwardly of the elasticized leg openings 24, 26, respectively.

As mentioned above, the elastic members 38 and 40 are maintained in a tension throughout the steps of applying the spiral patterns 36 of adhesive and folding the body contacting layer 16 to form the barrier cuffs 54 and 56. When the tension is released from the elastic members 38, 40, such as by cutting the body contacting layer 16 to length to form the finished disposable diaper, the elastic members 38, 40 "snap back" or return to their original length. In the course of returning to their original length, the elastic member 38, 40 forms gathers 52 in the barrier cuffs 54 and 56, respectively, at the location 49 where the adhesive patterns 36 were diverted onto the elastic members 38, 40 to affix them to the body contacting layer 16. In the presently preferred embodiment, these gathers 52 are located approximately in the center of the barrier cuffs 54 and 56, and help the diaper 12 to conform to the shape of the wearer as well as resist the passage of exudate material from the waste containment pocket 10 outwardly to the elasticized leg openings 24, 26.

Figure 5:
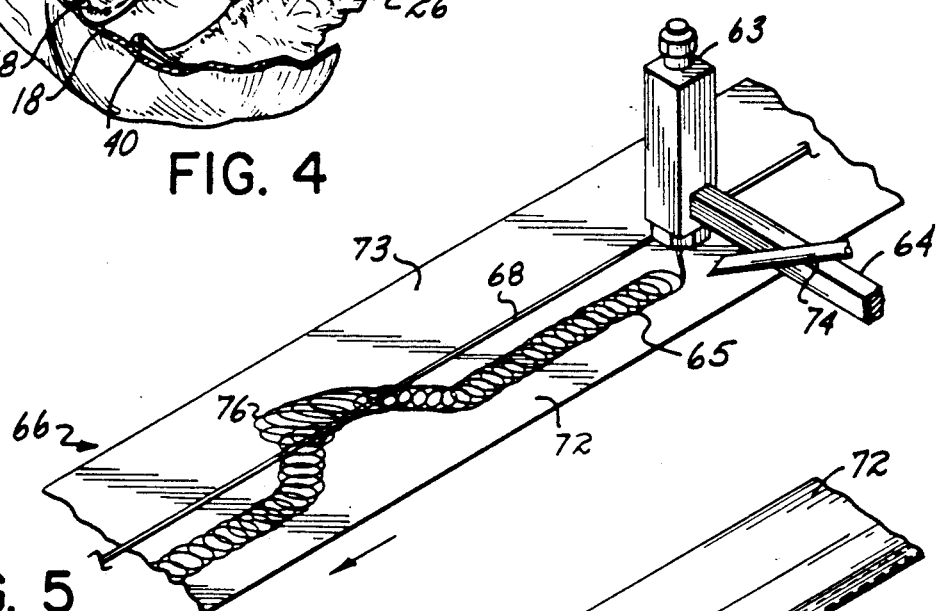
FIG. 5 is a schematic, perspective view of a dispensing device applying a pattern of adhesive onto a strip of material to form a single barrier cuff.
Figure 6:
FIG. 6 is the strip of material illustrated in FIG. 5 folded on itself to form one barrier cuff.

Referring now to FIGS. 5–8, an alternative embodiment of the method of this invention is illustrated wherein the waste containment pocket 10 of the disposable diaper 12 is defined by two identical barrier cuffs 60 which are adhered to the body contacting layer 16, but not integrally formed therewith. As shown in FIG. 5, a single dispensing device 63 identical to dispensing devices 30 and 32 and carried by a support 64 applies a spiral pattern 65 of adhesive onto a relatively narrow section or strip 66 of material such as the same type of non-woven material forming the body contacting layer 16, or another suitable material. An elastic member 68 of the same type as elastic members 38 and 40 is located in the middle of the strip 66 and maintained under tension thereon. The adhesive pattern 65 is applied to one side 72 of the strip 66 and extends substantially parallel to but not in contact with the elastic member 68 of the other side 73 of strip 66. An air tube 74, which is operated in the identical manner as air tubes 46 described above by a controller (not shown), intermittently diverts the adhesive pattern 65 onto the elastic member 68 and a portion of the side 73 of strip 66 at longitudinally spaced areas 76 therealong.

Figure 7:
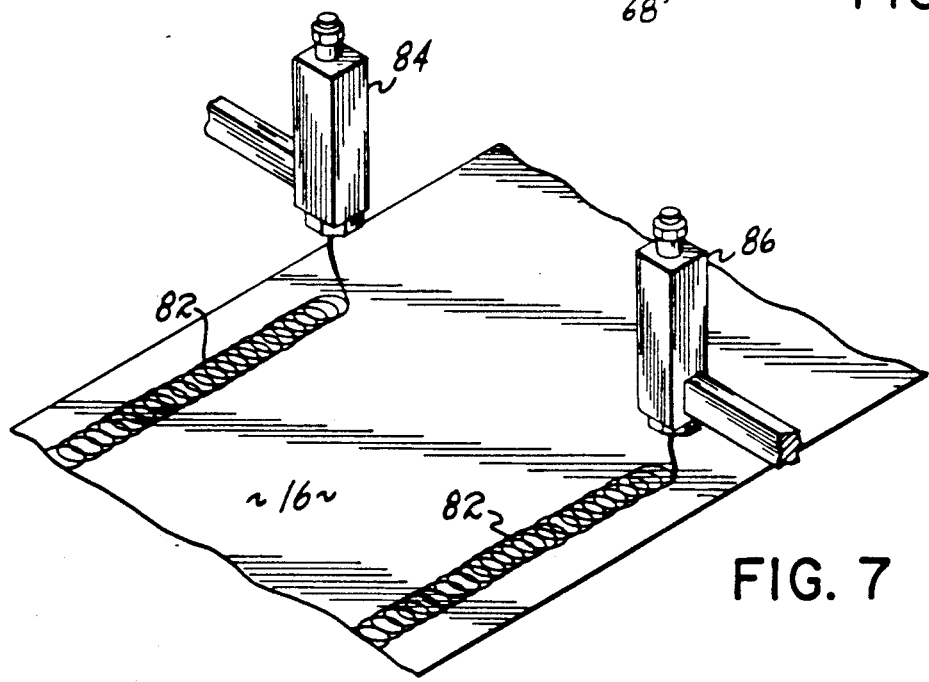
FIG. 7 is a schematic view of adhesive dispensers applying spaced patterns of adhesive onto the body contacting layer of a disposable garment.
Figure 8:
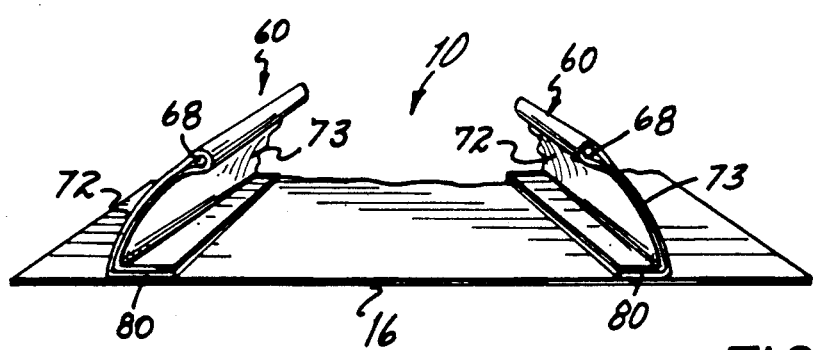
FIG. 8 is a schematic view of two barrier cuffs of the type shown in FIG. 6 which are adhered to a body contacting layer of a disposable garment along the adhesive patterns applied thereto in the step of FIG. 7.

The strip 66 is then folded in half so that its sides 72 and 73 adhere together and the elastic member 68 is captured therebetween to form the barrier cuff 60. Two barrier cuffs 60 are then attached to the surface of the body contacting layer 16 on opposite sides of the centerline 28 to define the waste containment pocket 10. As shown in FIGS. 7 and 8, the inner end of each barrier cuff 60 is folded to form a flap 80, and this flap 80 is brought into contact with one of the beads or patterns 82 of adhesive applied on opposite sides of the centerline of the body contacting layer 16 by suitable adhesive dispensers 84, 86 which are preferably of the same type as dispensers 30, 32 and 63. Alternatively, each individual barrier cuff 60 can be attached to the body contacting layer 16 by other means such as sonic bonding, the application of adhesive directly to flap 80 or the like. When the tension is released on the elastic member 68 of each barrier cuff 60, such as by cutting the body contacting layer 16 or strip 66 to length, pleats or gathers (not shown) are formed in each barrier cuff 78 as in the embodiment of FIGS. 1–4.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

For example, FIGS. 1, 2 and 5 illustrate an air tube 46 or 74 as one means for diverting or redirecting the path of the adhesive patterns 36 or 65 applied to the body contacting layer 16 or to the strip 66. It is contemplated that other means could be employed to divert the adhesive path such as a mechanism to intermittently move the adhesive dispensers 30, 32 and 63 perpendicularly relative to the direction of movement of the body contacting layer 16 or strip 66 to form longitudinally spaced areas 49 or 76 therealong where the adhesive bonds the elastic members 38, 40 or 68 to the body contacting layer 16 or strip 66.

Therefore, it is intended that the invention not be limited to the particular embodiment disclosed as the best mode contemplated for carrying out this invention, but that the invention will include all embodiments falling within the scope of the appended claims.

I claim:

1. The method of forming a waste containment pocket in a disposable garment, comprising:
   applying a first adhesive pattern onto a body contacting layer of the disposable garment in a path which is alongside but not in contact with a first elastic member maintained in tension atop said body contacting layer;
   intermittently diverting said path of said first adhesive pattern into contact with said first elastic member so that said body contacting layer and said first elastic member adhere together at spaced locations therealong;
   folding said body contacting layer on either side of said first elastic member upon itself to form a first barrier cuff which encloses said first elastic member;
   releasing said tension on said first elastic member to form gathers along said first barrier cuff at said spaced locations where said first elastic member is adhered to said body contacting layer;
   applying a second adhesive pattern onto the body contacting layer of the disposable garment in a path which is alongside but not in contact with a second elastic member maintained in tension atop said body contacting layer, said second elastic member being spaced from said first elastic member;

intermittently diverting said path of said adhesive pattern into contact with said second elastic member so that said body contacting layer and said second elastic member adhere together at spaced locations therealong;

folding said body contacting layer on either side of said second elastic member upon itself to form a second barrier cuff which encloses said second elastic member, said second barrier cuff being spaced from said first barrier cuff along said body contacting layer to form a waste containment pocket there-between;

releasing tension on said second elastic member to form gathers along said second barrier cuff at said spaced locations where said second elastic member is adhered to said body contacting layer.

2. The method of claim 1 in which the steps of applying said first and second adhesive patterns onto the body contacting layer each comprise applying an elongated thin strand or fiber of adhesive in a swirling, spiral pattern onto the body contacting layer.

3. The method of claim 1 in which said steps of applying said first and second adhesive patterns onto the body contacting layer each comprise applying a longitudinally extending adhesive pattern substantially parallel to but not in contact with each of said first and second elastic members.

4. The method of claim 1 in which said steps of applying said first and second adhesive patterns each comprises dispensing an elongated adhesive fiber in a spiral motion from an adhesive dispenser spaced above said body contacting layer of the disposable garment along one side of each said first and second elastic members.

5. The method of claim 4 in which said steps of intermittently diverting said first and second adhesive patterns each comprise impacting said elongated adhesive fiber discharged from said adhesive dispenser with a jet of air before said adhesive fiber contacts the body contacting layer of the disposable garment so that said elongated adhesive fiber is diverted onto said first or second elastic member.

6. The method of claim 4 in which said steps of intermittently diverting said first and second adhesive patterns each comprise impacting said elongated adhesive fiber discharged from said adhesive dispenser with a jet of air before said adhesive fiber contacts the body contacting layer of the disposable garment so that said elongated adhesive fiber forms an enlarged spiral pattern which is diverted from said one side of each said first and second elastic members onto said first and second elastic members and onto a portion of the body contacting layer on the opposite side of each said first and second elastic members.

7. The method of forming a waste containment pocket in a disposable garment, comprising:

forming a first barrier cuff and a second barrier cuff, each of said first and second barrier cuffs being formed by:

(i) applying an adhesive pattern onto a strip of material in a path which is alongside but not in contact with an elastic member maintained in tension atop said strip of material;

(ii) intermittently diverting said path of said adhesive pattern onto said elastic member so that said strip of material and said elastic member adhere together at spaced locations therealong;

(iii) folding said strip of material in half so that said elastic member is enclosed within the two halves of said strip of material and said halves are adhered together to form a barrier cuff;

(iv) releasing said tension on said elastic member to form gathers along said barrier cuff where said elastic member is adhered thereto;

attaching said first barrier cuff and said second barrier cuff on opposite sides of the center of the body contacting layer of the disposable garment to form a waste containment pocket therebetween.

8. The method of claim 7 in which the step of applying an adhesive pattern to the strip of material comprises applying an elongated adhesive fiber in a swirling, spiral pattern onto the strip of material.

9. The method of claim 7 in which said step of applying said adhesive pattern onto said strip of material comprises applying a longitudinally extending adhesive pattern substantially parallel to but not in contact with said elastic member.

10. The method of claim 7 in which said step of applying said adhesive pattern comprises discharging an elongated adhesive fiber in a spiral motion from an adhesive dispenser spaced above said body contacting layer of the disposable garment onto one half of said strip alongside said elastic member.

11. The method of claim 10 in which said step of intermittently diverting said path of said adhesive pattern comprises impacting said elongated adhesive fiber discharged from said adhesive dispenser with a jet of air before said elongated adhesive fiber contacts the strip of material so that said elongated adhesive fiber is diverted onto said elastic member.

12. The method of claim 10 in which said step of intermittently diverting said path of said adhesive pattern comprises impacting said elongated adhesive fiber discharged from said adhesive dispenser with a jet of air before said elongated adhesive fiber contacts the strip of material so that said elongated adhesive fiber forms an enlarged spiral pattern which is diverted from said one half of said strip onto said elastic member and onto said other half of said strip.

13. The method of claim 7 in which said step of attaching said first and second barrier cuffs to said body contacting layer comprises applying an elongated adhesive fiber in a spiral pattern onto one of said body contacting layer and said first and second barrier cuffs, and then bringing said first and second barrier cuffs and said body contacting layer into contact with one another.

* * * * *